United States Patent [19]

Ohmoto et al.

[11] Patent Number: 5,330,894
[45] Date of Patent: Jul. 19, 1994

[54] ANTI-PROCOLLAGENASE MONOCLONAL ANTIBODIES AND A METHOD FOR THE ASSAY OF PROCOLLAGENASE UTILIZING THEREOF

[75] Inventors: Hiroshi Ohmoto, Osaka; Shintaro Inoue, Odawara; Seiichi Iwamoto, Kobe, all of Japan

[73] Assignee: Kanebo, Ltd., Tokyo, Japan

[21] Appl. No.: 768,866

[22] PCT Filed: Feb. 7, 1991

[86] PCT No.: PCT/JP91/00144
§ 371 Date: Sep. 27, 1991
§ 102(e) Date: Sep. 27, 1991

[87] PCT Pub. No.: WO91/12333
PCT Pub. Date: Aug. 22, 1991

[30] Foreign Application Priority Data

Feb. 7, 1990 [JP] Japan ................................. 2-28098

[51] Int. Cl.$^5$ .......................................... G01N 33/573
[52] U.S. Cl. ................................... 435/7.4; 435/7.92; 435/7.94; 435/23; 436/518; 436/813; 530/391.1; 530/391.3
[58] Field of Search ............. 435/7.4, 7.97, 7.94, 435/23; 436/518, 813; 530/391.1, 391.3

[56] References Cited

U.S. PATENT DOCUMENTS 4,376,110 3/1983 David et al. ..................... 436/513

OTHER PUBLICATIONS

Bergmann et al., *J. Clin. Chem. Clin. Biochem.*, vol. 27, pp. 351–359. (1989).
Birkedal-Hansen et al., "Monoclonal Antibodies to Human Fibroblast, etc." Biochemistry 1988, 27, 6751–6758.
Birkedal-Hasen et al., "Use of Inhibitory (Anti--Catalytic) Antibodies, etc.", Immunological Investivations, 18 (1–4), 211–224 (1989).
Crespo et al., "Monoclonal Antibodies Against Synovial Collagenase, etc." Collagen Rev. Res. vol. 1/1988, pp. 1–10.
Petersen et al., "Production of Procollagenase by Cultured Human Keratinocytes", The Journal of Bio. Chem., vol. 262, No. 2, pp. 835–840 (1987).

*Primary Examiner*—Toni R. Scheiner
*Assistant Examiner*—Susan C. Wolski
*Attorney, Agent, or Firm*—Millen, White, Zelano & Branigan

[57] ABSTRACT

A monoclonal antibody against a procollagenase with a molecular weight of 52000 whose corresponding collagenase cleaves Type I, Type II and Type III collagens, the monoclonal antibody being characterized in, (a) that it belongs to the immunoglobulin class and subclass of $G_1$ and its L-chain isotype is kappa, and, (b) that it has an inhibitory activity on the collagenase that cleaves Type I, Type II and Type III collagens, and a method for the assay of procollagenase by enzymeimmunoassay utilizing thereof.

2 Claims, 1 Drawing Sheet

ANTI-PROCOLLAGENASE MONOCLONAL ANTIBODIES AND A METHOD FOR THE ASSAY OF PROCOLLAGENASE UTILIZING THEREOF

TECHNICAL FIELD

The present invention relates novel monoclonal antibodies against a procollagenase whose corresponding collagenase cleaves Type I, Type II and Type III collagens, and a method for the assay of the procollagenase by enzymeimmunoassay utilizing thereof.

BACKGROUND ART

Collagenase, the enzyme which cleaves collagens, is widely distributed in organisms.

Since an elevated collagenase activity is noted in pathological tissues such as synovialis in rheumatoid arthritis, ulcerated cornea and osteoma tissues, it is beneficial to determine collagenase activity in pathological tissues and in body fluids for diagnosis of such disorders.

Collagenase is produced in a latent (inactive) form, procollagenase, and both of collagenase and procollagenase occur in tissues. Therefore, for the assay of collagenase activity, procollagenase has to be activated by a pretreatment with a protease such as trypsin or with a mercurial compound, etc. Moreover, as a large quantity of inhibitors of collagenase activity is present in tissues, a very complicated procedure is required in order to eliminate these inhibitors.

Several types of collagenases are known according to the types of their collagen substrates, and they are classified into the collagenase that cleaves type I, type II and type III collagens (interstitial collagens) (hereinafter referred to as interstitial collagenase), the collagenase that cleaves type IV collagen and type V collagen, and the like.

With regard to the monoclonal antibodies against the procollagenase of the interstitial collagenase (hereinafter referred to as "interstitial procollagenase"), 11 monoclonal antibodies have been disclosed, which were prepared by using as antigens a mixture of the interstitial procollagenases having a molecular weight of 52000 and 57000 [see Biochemistry, 27, 6751 (1988)]. However, the monoclonal antibodies of the present invention, which belong to the immunoglobulin in class and subclass $G_1$, whose L-chain isotype is kappa and which have a collagenase inhibiting activity, have never been disclosed before.

DISCLOSURE OF INVENTION

Disclosure of Invention

Figure 1:
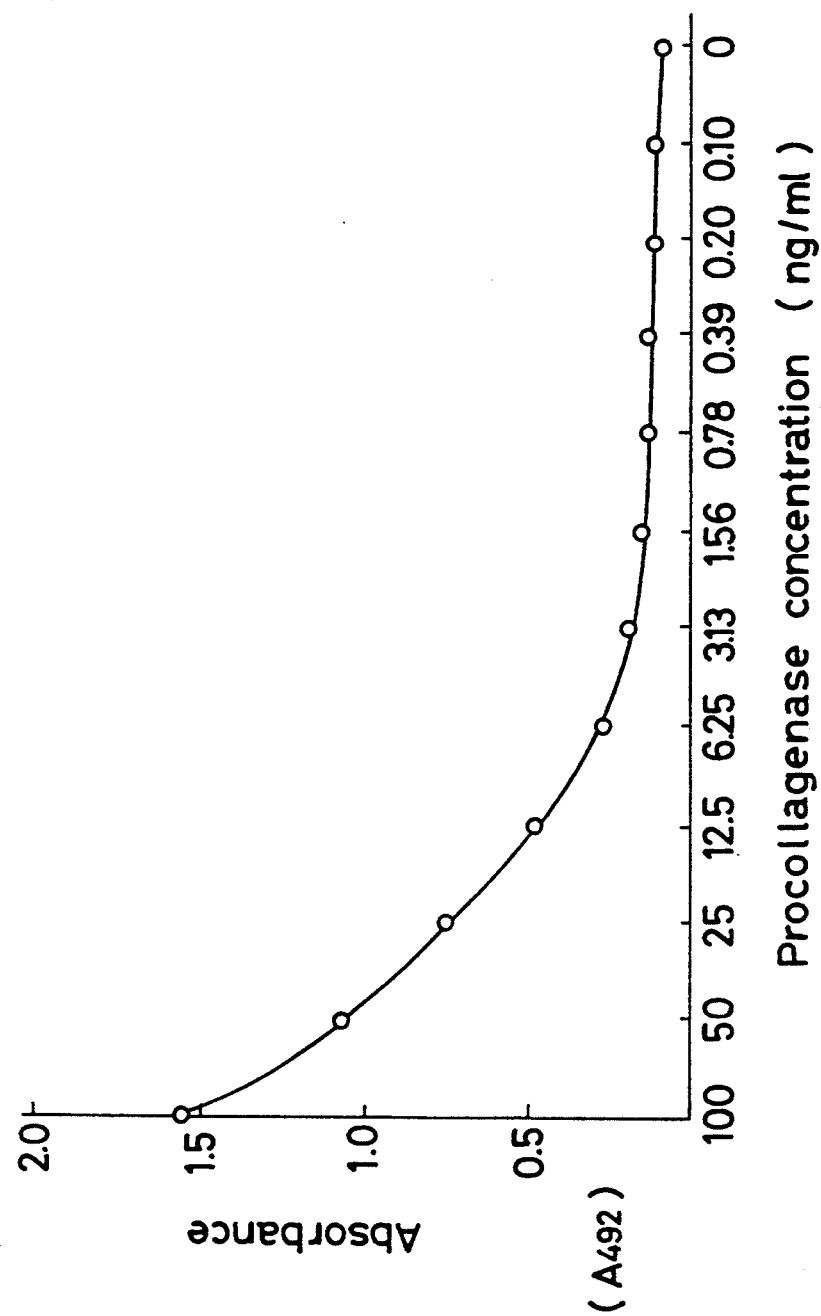
FIG. 1 illustrates an analytical curve from the assay of procollagenase utilizing antibody FERM BP-2701 (K5E1) as the immobilized monoclonal antibody and antibody FERM BP-2700 (K2F7) as the biotinylated anti-procollagenase monoclonal antibody.

The inventors have prepared novel monoclonal antibodies against a interstitial procollagenase having a molecular weight of 52000, and established a simple method for the assay of procollagenase by enzymeimmunoassay utilizing said antibodies, and then determined the concentration of procollagenase in human serum by the method. As the results, the inventors have found that the serum procollagenase concentration is significantly higher in patients of cancer rheumatoid arthritis (hereinafter abbreviated to "RA") and osteoarthritis (hereinafter abbreviated to "OA") than that in normal subjects, and thus accomplished the present invention.

It is an object of the present invention to provide novel monoclonal antibodies against a interstitial procollagenase. Another object of the present invention is to provide a simple method for the assay of the procollagenase by enzymeimmunoassay utilizing the novel monoclonal antibodies.

Determination of the procollagenase concentration in human serum using the assay method of the present invention is of great advantage in diagnosis of patients' disorders with elevated collagenase activity, such as cancer, RA, OA and the like.

Described below are the method for preparation of the monoclonal antibodies of the present invention and the method for the assay of a procollagenase by enzymeimmunoassay using said antibodies.

Described first is the method for preparation of the monoclonal antibodies of the present invention.

The monoclonal antibodies of the present invention may be obtained through the following process, (1) to (6).

(1) Preparation of the interstitial procollagenase (antigen) having a molecular weight of 52000

The interstitial procollagenase having the molecular weight of 52000, which is used for the preparation of the monoclonal antibodies of the present invention, may be prepared by separation and purification from the culture medium of either HT1080-SF2 cells, which are derived from human fibrosarcoma cells HT1080 (ATCC CCL 121) and can grow in a serum-free, protein-free medium [see SEITAI NO KAGAKU, 37(4), 271(1986)], or, likewise, "human fibrosarcoma HT-P12-4, accession No. FERM P-10912, Fermentation Research Institute, Agency of Industrial Science and Technology", which are obtained by a long-term culture of human fibrosarcoma cells HT1080 (ATCC CCL 121) in a serum-free, protein-free medium and can grow in a serum-free, protein-free medium.

The culture of above cells is performed by allowing the cells to stand for at least 4 days, preferably 7 to 14 days, in a HAM-F12 medium containing EAGLE'S amino acid-vitamin medium at 35° to 37° C.

The separation and purification of procollagenase is performed first by column chromatography of the supernate of the culture medium on a cation exchanger such as CM-Sepharose CL-6B (trademark; from PHARMACIA), and then by column chromatography on zinc chelating Sepharose 6B (trademark; from PHARMACIA).

As the eluant for the first column chromatography, a Tris-HCl buffer solution containing $CaCl_2$ and a non-ionic surfactant and a Tris-HCl buffer solution (pH 7.8) containing $CaCl_2$, a non-ionic surfactant and NaCl are used. The procollagenase is eluted with a linear NaCl gradient.

As the eluant for the second column chromatography, an acetic acid buffer solution (pH 4.8) containing Nacl, $CaCl_2$ and non-ionic surfactant such as polyoxyethylene lauryl ether and a 2-(morpholino)ethanesulfonic acid monohydrate buffer solution (pH about 6.8) containing NaCl, $CaCl_2$ and a non-ionic surfactant are used. The column is developed with a pH gradient (gradually lowering pH.)

(2) Preparation of antibody-producing spleen cells

Mice, for example BALB/c mice, preferably BALB/c mice of 6-week old or over, are immunized by administering an emulsion consisting of the procollagenase obtained above and an adjuvant such as Freund's adjuvant. The spleen is then removed and the antibody-producing spleen cells are prepared.

The immunization is made by administering the antigen, procollagenase, usually 3 times or more. The amount administered at a time is 1 to 1000 μg/mouse. Usually, the antigen is made into a solution of the concentration of 20 to 1000 μg/ml, and this is mixed with the equivalent volume of an adjuvant, such as Freund's adjuant, and then the mixture is administered.

After immunization, the spleen of the mouse is excised, and the cells are dispersed in the Dulbecco's modified EAGLE'S minimum essential medium (hereinafter abbreviated to "DMEM") to obtain a suspension of the antibody-producing spleen cells.

(3) Preparation of myeloma cells

8-Azaguanine resistant myeloma cells, for example the commercially available myeloma cells of mouse origin P3X63Ag8U.1 (hereinafter abbreviated to "P3U1"), Sp2/O-Ag14, P3X63-Ag8.653 (all marketed by DAINIPPON SEIYAKU) and the like, are used.

Under the air containing 5 to 10 v/v % $CO_2$ at 37° C., the myeloma cells are cultured in a medium containing about 100 μM 8-azaguanine, for example an RPMI 1640 medium supplemented with 5 to 20 v/v % of fetal bovine serum or a DMEM medium supplemented with 5 to 20 v/v % of fetal bovine serum, then washed with the medium containing no 8-azaguanine, and used in the following cell fusion process.

(4) Cell fusion and selection of hybridomas producing anti-procollagenase antibodies.

Aforementioned antibody-producing spleen cells and myeloma cells are subjected to a treatment for cell fusion, and the hybridomas producing antiprocollagenase antibodies are selected.

The treatment for cell fusion is performed by mixing the suspension of the antibody-producing spleen cells with the suspension of the myeloma cells, and then for example, either by eliminating the supernate by a slow-rate centrifugation to obtain the mixture of both cells, adding to this a polyethylene glycol (hereinafter abbreviated to "PEG"), stirring and agitating according to the method described in Nature, 266, 550 (1977), or by mixing the antibody-producing spleen cells and the myeloma cells with a PEG solution and then centrifuging the mixture at a slow-rate according to the method described in Somatic Cell Genetics, 3, 231 (1977).

PEG has a mean molecular weight of, preferably, 1000 to 6000, and it is used at a concentration of, preferably, 30 to 50 w/v % in a mixture solution with DMEM medium.

Mixing ratio of the antibody producing spleen cells to the myeloma cells is preferably such that the antibody producing spleen cells are used 1 to 20 times as much as the myeloma cells.

Then, the cell mixture after the cell fusion treatment as above is suspended in a medium which allows only the hybridomas to grow, for example HAT medium (a medium containing hypoxanthine, aminopterin and thymidine), at about $1 \times 10^6$ cells/ml, and the suspension is injected into each well of a microplate and cultured for 10 to 14 days under the air containing 5 to 10 v/v % of $CO_2$ at 37° C., including an exchange of the medium on, usually, the 4th day.

Then the supernate of the culture in the wells containing grown cells is measured by enzymeimmunoassay using procollagenase as an immobilized antigen and an enzyme-labeled anti-mouse immunoglobulin, and the wells in which anti-procollagenase antibodies have been produced are selected.

(5) Cloning and selection of hybridomas

The hybridomas in the wells selected as above are cloned by, for example, limiting dilution with HAT medium (see HYBRIDOMA TECHNIQUES EMBO Course 1980, Basel), and the wells which contain a single clone producing an anti-procollagenase monoclonal antibody are selected by testing the supernate of the culture medium by enzymeimmunoassay as aforementioned, and thus cloned hybridomas producing the anti-procollagenase monoclonal antibodies are obtained.

(6) Production and selection of monoclonal antibodies

Then, each hybridoma is either cultured to separate and purify the monoclonal antibody from the culture medium or transplanted in the peritoneal cavity of an animal to allow it to proliferate and then to separate and purify the monoclonal antibody from the ascites. The monoclonal antibody is then tested for immunological classification and measured for the inhibitory activity on the interstitial collagenase to select the monoclonal antibodies of the present invention as well as the hybridomas producing them.

The culture of the hybridoma is carried out in a conventional medium, for example an RPMI 1640 medium supplemented with 5 to 20 v/v % of fetal bovine serum or a DMEM medium supplemented with 5 to 20 v/v % of fetal bovine serum, for 3 days to 3 weeks, preferably for 10 to 14 days while transferring the cells into the fresh medium mentioned above every 3 days.

The proliferation of the hybridoma in the peritoneal cavity of the animal is allowed by transplanting the hybridoma into the peritoneal cavity of a mammalian animal compatible with the hybridoma, such as BALB/c mouse, and keeping the animal for 1 to 2 weeks.

The purification of the monoclonal antibody is carried out by centrifuging the above culture medium or ascites, and, for example salting out the obtained supernate with ammonium sulfate or subjecting it to an ion exchange chromatography.

For the salting out with ammonium sulfate, 30 to 50% saturated ammonium sulfate is preferably used. The monoclonal antibody salted out is then dialyzed against pH 7.4 phosphate-buffered saline (hereinafter abbreviated to "PBS").

The ion exchange chromatography is preferably performed on column chromatography using an anion exchanger resin such as DEAE Sepharose (trademark; from PHARMACIA). Usually, a Tris buffer solution, pH about 7, is used as an eluant to obtain the solution of the monoclonal antibody.

The test for immunological classification of the monoclonal antibody is performed by enzymeimmunoassay using anti-mouse immunoglobulin antibody as an immobilized antibody, and thus the class, subclass and L-chain isotype of the anti-procollagenase monoclonal antibody are determined.

The assay of the inhibitory activity of the monoclonal antibody on the interstitial collagenase is performed by mixing the anti-procollagenase monoclonal antibody and a known amount of the collagenase, allowing to react for 10 minutes at 35° C., and measuring the collagenase activity according to the method described in Japanese Journal of Inflammation, 4, 123 (1984) (hereinafter referred to as "the method of Nagai et al."). The concentration of the monoclonal antibody required to inhibit the collagenase activity by 50% ($IC_{50}$) is thus determined.

Thus, the following 11 novel anti-procollagenase monoclonal antibodies (hereinafter referred to as K5E1, K2F7, K1C2, K1F12, K2C3, K3B2, K3F10, K4B4, K4F5, K4H11 and K5G5) and the corresponding hybridomas producing these monoclonal antibodies were obtained.

The class, subclass, L-chain isotype and collagenase inhibiting activity ($IC_{50}$) of the monoclonal antibodies are shown in Table 1.

TABLE 1

| Monoclonal antibody | Immunoglobulin class and subclass/L-chain isotype | $IC_{50}$ (ng/ml) |
|---|---|---|
| K5E1 | $G_1$/kappa | 2.5 |
| K2F7 | $G_1$/kappa | 2.7 |
| K1C2 | $G_1$/kappa | 830 |
| K1F12 | $G_1$/kappa | 10.6 |
| K2C3 | $G_1$/kappa | 5.4 |
| K3B2 | $G_1$/kappa | 1.9 |
| K3F10 | $G_1$/kappa | 25.0 |
| K4B4 | $G_1$/kappa | 59.5 |
| K4F5 | $G_1$/kappa | 5.2 |
| K4H11 | $G_1$/kappa | 4.3 |
| K5G5 | $G_1$/kappa | 3.6 |

The K5E1-producing hybridoma indicated as "Anti-procollagenase monoclonal antibody (K5E1) producing hybridoma" and the K2F7-producing hybridoma indicated as "Anti-procollagenase monoclonal antibody (K2F7) producing hybridoma" were deposited, respectively, with Fermentation Research Institute, Agency of Industrial Science and Technology, of 1-3, Higashi 1-chome, Tsukuba-shi, Ibarakiken, 305 Japan, on Dec. 25, 1989. The accession of the "Anti-procollagenase monoclonal antibody (K5E1) producing hybridoma" is FERM BP-2701, and the accession number of the "Anti-procollagenase monoclonal antibody (K2F7) producing hybridoma" is FERM BP-2700.

The assay method of procollagenase according to the present invention is described hereunder.

The assay method of procollagenase according to the present invention may be applied in determining the concentration of procollagenase in human body fluids, particularly the serum, by enzymeimmunoassay using the monoclonal antibodies of the present invention obtained as above.

An enzymeimmunoassay may be performed according to a conventional method, preferably the sandwich method.

The method for the assay of procollagenase of the present invention is described hereunder according to the sandwich method.

The immobilized antibody is prepared by immobilizing the monoclonal antibody of the present invention on such carriers as a microplate, beads, a stick or a test tube made of polystyrene, polycarbonate, polypropylene or polyvinylchloride according to the conventional method such as adsorption method or cross-linking method.

An enzyme-labeled antibody to be used in the sandwich method may be prepared according to a known method using the monoclonal antibody of the present invention, biotin or an enzyme, such as horseradish peroxidase, alkaline phosphatase, $\beta$-galactosidase and the like, and a cross-linking agent, such as known maleimide derivatives, pyridyl disulfide derivatives and the like. For example, a biotin-labeled antibody may be prepared according to the method described Journal of Clinical Microbiology, 20, 109 (1984). A horseradish peroxidase-labeled antibody may be prepared according to the method described p.215 of Immunofluorescence and Related Staining Techniques, ed. by W. Knapp, Elsevier, Amsterdam, 1978.

In regard with the combination of an immobilized antibody and a labeled antibody, it is preferred to use a combination of such monoclonal antibodies that recognize different epitopes from each other and may allow a sensitive assay of procollagenase. A preferable combination of monoclonal antibodies is selected according to the method below.

The combination of monoclonal antibodies that recognize different epitopes from each other may be determined by selecting monoclonal antibodies which do not compete with each other in competitive enzymeimmunoassay in which an immobilized procollagenase is reacted with a biotin-labeled anti-procollagenase monoclonal antibody [the method for labeling is in accordance with the method described in Journal of Clinical Microbiology, 20, 109 (1984)] and 20 times as much amount of an anti-procollagenase monoclonal antibody.

A combination of monoclonal antibodies which may allow a sensitive assay of procollagenase may be selected by evaluating the assay sensitivity on an analytical curve which can be obtained from the assay of a known amount of procollagenase by sandwich immunoassay using the monoclonal antibodies selected above as an immobilized antibody or a labeled antibody, respectively.

Among the monoclonal antibodies of the present invention, those having an aforementioned collagenase inhibiting activity ($IC_{50}$) of less than 10 ng/ml are suitably used as immobilized antibodies.

The example of the preferred combinations of the monoclonal antibodies of the present invention [indicated as (antibody used as the immobilized antibody, antibody used as the labeled antibody)] include, (K5E1, K2F7), (K4H11, K2F7), (K4H11, K3B2), (K4H11, K3F10), (K4H11, K4B4), (K4F5, K4H11), (K4F5, K3F10), (K5G5, K4H11), (K5G5, K1C2), (K5G5, K1F12), (K2F7, K1F12), (K2F7, K3F10), (K2F7, K4H11), (K5E1, K4B4) and (K5E1, K4F5), and the use of K5E1 as the immobilized antibody and K2F7 as the labeled antibody is particularly preferred for it enables a sensitive assay of procollagenase.

BEST MODE FOR CARRYING OUT THE INVENTION

The present invention is described in further detail below according to the examples.

In the examples, the determination of class, subclass and L-chain isotype of the monoclonal antibodies and the determination of collagenase inhibiting activity of the monoclonal antibodies were carried out according to the following method.

The method for Determination of Class, Subclass and L-chain Isotype of the Monoclonal Antibodies:

The antibodies to each class and subclass of mouse immunoglobulin (IgA, IgM, $IgG_1$, $IgG_{2a}$, $IgG_{2b}$ and $IgG_3$) and the antibodies to the L-chain (kappa and lamda) (all from MILES) were diluted respectively to 5 $\mu$g/ml with a 0.05M sodium carbonate-sodium bicarbonate buffer solution (pH 9.6), and 100 μl each of the solutions was injected into each well of a 96-well microplate (Immulon 600) and stored overnight at 4° C. to immobilize the antibodies in the wells of the microplate.

Each well was washed with a washing solution consisting of a PBS (pH 7.4) containing 0.05 v/v % of Tween-20 (polyoxyethylene sorbitan mono-laurate) hereinafter abbreviated to "T-PBS"), then 300 μl of a PBS (pH 7.4) containing 0.5 w/v % of bovine serum albumin (hereinafter abbreviated to "BSA": from WAKO JUNYAKU K.K.) was added, allowed to stand for 1 hour and the supernate was removed.

Then, each monoclonal antibody was diluted to 1μg/ml with a PBS (pH 7.4) containing 0.1 w/v % of BSA, and 100 μl of the solution was added into each well, allowed to react for 2 hours at room temperature, and then the well was washed with T-PBS (pH 7.4).

Then, a biotin-labeled anti-mouse immunoglobulin (from ZYMED) was diluted to 5 μg/ml with a PBS (pH 7.4) containing 0.1 w/v % of BSA, and 100 μl each of this solution was added into each well, allowed to react for 1 hour at room temperature, and the well was washed with T-PBS (pH 7.4).

Then, streptavidin-peroxidase (from AMERSHAM) was diluted 1000 times with a PBS (pH 7.4) containing 0.1 w/v % of BSA, and 100 μl each of the solution was added into each well, allowed to react for 30 minutes at room temperature, and the well was washed with T-PBS.

Then, 100 μl each of a 0.15M citric acid-sodium phosphate buffer solution (pH 5.0) containing hydrogen peroxide and o-phenylenediamine (the former 0.015 w/v %, the latter; 0.2 mg/ml) was added into each well, allowed to react for 5 minutes at room temperature, and the reaction was stopped by the addition of 50 μl of 5N sulfuric acid into each well.

The absorbance at 492 nm of the solution thus obtained was measured using a Corona 2-wavelength microplate photometer (MTP-22, from CORONA DENKI K.K.), and reactivity of each monoclonal antibody with the antibodies to mouse immunoglobulins of each class and subclass (IgA, IgM, $IgG_1$, $IgG_{2a}$, $IgG_{2b}$ or $IgG_3$) and to the antibodies to the L-chain (kappa or lamda) was evaluated, respectively, from the corresponding adsorbance, and thus the class, subclass and L-chain isotype of the monoclonal antibody was determined.

The Method for the Assay of Collagenase Inhibiting Activity of the Monoclonal Antibodies:

To 50 μl of a standard collagenase solution (0.7 unit/ml) was added at 35° C. 50 μl of a solution of the anti-procollagenase monoclonal antibody diluted with a buffer solution for assay (50 mM Tris-HCl buffer solution containing 0.2M NaCl, 5 mM $CaCl_2$, 0.05 v/v % of Brij-35 and 0.02 w/v % of $NaN_3$). 10 minutes later, to the mixture solution was added 100 μl of a solution of type I collagen from bovine labeled with fluorescein isothiocyanate [0.5 mg/ml, prepared by twofold dilution of FITC-collagen (solution in 0.01N acetic acid) from COSMOBIO with a 100 mM Tris-HCl buffer solution (pH 7.5) containing 0.4M NaCl, 10 mM $CaCl_2$ and 0.04 w/v % of $NaN_3$] as the substrate, and the collagenase activity in the mixture solution was determined according to the method of Nagai et al. The test was performed on solutions which differed in concentration of the anti-procollagenase monoclonal antibody, and, from the regression curve drawn according to the relationship between the amount of the anti-procollagenase monoclonal antibody and the collagenase activity, the concentration of the antiprocollagenase monoclonal antibody at which the activity of the standard collagenase solution was inhibited by 50% [$IC_{50}$ (ng/ml)] was determined.

In the above, the standard collagenase solution was prepared by activating the procollagenase solution in Example 1-(1) below by trypsin (type 12, from SIGMA) according to the method of Nagai et al., then inactivating trypsin by soybean trypsin inhibitor (from MERCK), determining the collagenase activity according to the method of Nagai et al., and then adjusting to 0.7 unit/ml with the buffer solution for assay.

EXAMPLE 1

Production of Monoclonal Antibodies:

The monoclonal antibodies of the present invention was obtained according to (1) to (6) below.

(1) Preparation of the interstitial procollagenase (antigen) having a molecular weight of 52000

$1.8 \times 10^8$ of the anchorage-independent cells ("Human fibrosarcoma HT-P12-4"; accession No, FERM P-10912. Fermentation Research Institute, Agency of Industrial Science and Technology), which are derived from human fibrosarcoma cells HT 1080 and can grow in a serum-free, protein-free medium, were suspended in 180 ml of a HAM-F12 medium containing 1.76 g/l of the EAGLE'S amino acid-vitamin powder medium (from NISSUI SEIYAKU K.K.), and 60 ml each of the suspension was cultured for 14 days at 37° C. The culture supernate was collected and stored at −80° C.

Total 160 ml of the culture supernate obtained above was made to 400 ml with a 10 mM Tris-HCl buffer solution containing 1 mM $CaCl_2$ and 0.05 v/v % of Brij-35 (adjusted to pH 7.8 at 4° C., hereinafter abbreviated to "CM-A buffer solution") , and loaded on a column (2.46 cm × 18 cm, bed volume; 85 ml) charged with CM-Sepharose CL-6B (trademark; from PHARMACIA) and equilibrated with CM-A buffer solution. After the column was sufficiently washed with the same buffer solution, the fractions containing procollagenase (NaCl, 0.3 to 0.5M) were obtained at a flow rate of 40 ml/h with a linear NaCl gradient using 250 ml each of CM-A buffer solution and a CM-A buffer solution containing 0.7M NaCl, The fraction was concentrated approximately 8 fold with YM-5 membrane (from AMICON) to obtain a clude procollagenase solution (approximately 600 μg/ml). The solution was loaded on a column (1.2 cm × 16 cm, bed volume 18 ml) charged with zinc chelating Sepharose 6B (trademark; from PHARMACIA) sufficiently equilibrated with a 50 mM 2-(morpholino)ethanesulfonic acid monohydrate buffer solution (adjusted to pH 6.8 with Tris at 4° C., hereinafter abbreviated to "MES-A buffer solution") containing 0.5M NaCl, 1 mM $CaCl_2$ and 0.05 v/v % of Brij-35. After sufficiently washed with the MES-A buffer solution, tile column was developed at a flow rate of 13 ml/h with a pH gradient using a 45 ml of the MES-A buffer solution and a 45 ml of an acetic acid buffer solution containing 0.5M NaCl, 1 mM $CaCl_2$ and 0.05 v/v % of Brij-35 (adjusted to pH 4.8 with Tris at 4° C.; hereinafter abbreviated to "the acetic acid buffer solution"). Procollagenase fraction was eluted as a sharp peak when the pH of the eluant reached about 5.3. The fraction was collected to obtain about 6 ml of a procollagenase solution (approximately 300 μg/ml). Analysis of it by sodium dodecyl sulfate polyacrylamide gel electrophoresis exhibited a single band at a molecular weight of 52000.

(2) Preparation of the antibody-producing spleen cells

133 μl of the crude procollagenase solution obtained in (1) above (containing about 68 μg of procollagenase) was mixed with the equal amount of Freund's complete adjuvant (from DIFCO) to prepare an emulsion. Then about 250 μl of this emulsion was administered subcutaneously to BALB/c mice (9 weeks old), and about 10 μl of it into the foot pad, respectively, for initial immunization. On the 14th and 36th days after it, the emulsion prepared from the crude procollagenase solution and Freund's incomplete adjuvant (from DIFCO) was likewise administered twice for additional immunization. On the 14th day after the second additional immunization, 200 μl of a physiological saline containing about 10 μg of the above procollagenase solution was intravenously administered for the final immunization.

3 days later, the mice were sacrificed and the spleen was aseptically removed. The removed spleen was cut into fine pieces with scissors in DMEM medium, passed through a mesh to form a suspension of single cells, and washed 3 times with DMEM medium to prepare a 10 ml suspension of the antibody-producing spleen cells in DMEM medium (containing $9.3 \times 10^7$ cells).

(3) Preparation of myeloma cells

Mouse myeloma cells P3U1 (ATCC CRL-1597, $5 \times 10^6$ cells) was added to a 25 ml of the following RPMI 1640 medium containing 100 μM 8-azaguanine and 10 v/v % of fetal bovine serum, and cultured for 5 days at 37° C. under the air containing 5 v/v % of $CO_2$, and washed twice with DMEM medium to prepare 10 ml of a suspension of the mouse myeloma cells P3U1 in DMEM medium (containing $1.0 \times 10^8$ cells).

Method for Preparation of RPMI 1640 Medium:

10.4 g of RPMI 1640 (from GIBCO), 1.3 g of sodium bicarbonate, 25.2 mg of L-glutamine, 63.5 mg of penicillin G, 100 μmg of streptomycin sulfate, 10 mg of tylosine and 40 μl of 2-mercaptoethanol (from WAKO JUNYAKU K.K.) were admixed with distilled water to make 1000 ml, and the solution was subjected to filter sterilization through a 0.45 μm membrane filter (from TOYO ROSHI K.K.) to prepare the medium.

(4) Cell fusion and selection of hybridomas producing the anti-procollagenase antibodies 10 ml of the suspension of the antibody-producing spleen cells ($9.3 \times 10^7$ cells) and 0.93 ml of the suspension of mouse myeloma cells P3U1 ($9.3 \times 10^6$ cells) obtained in (2) and (3) above, respectively, were mixed in a 50 ml centrifugation tube and centrifuged for 10 minutes at 1000 rpm to precipitate the mixture of both cells. After removing the supernate, 0.5 ml of a DMEM medium containing polyethylene glycol 1000 and dimethylsulfoxide (hereinafter abbreviated to "DMSO") (their content was 42.5 w/v % and 15 v/v %, respectively) was added dropwise to the mixture of the both cells within 1 minute while gently stirring.

Then, 1 ml, 1 ml, 5 ml, 5 ml and then 10 ml of the DMEM medium were successively added dropwise within 1 minute, respectively, while gently stirring to attain cell fusion treatment.

Then, the supernate was removed after a centrifugation for 10 minutes at 1000 rpm and thus a mixture of fusion-treated cells was obtained.

The mixture was suspended in HAT medium (a RPMI 1640 medium containing 100 μM of hypoxanthine, 0.4 μM of aminopterin, 16 μM of thymidine and 10 v/v % of fetal bovine serum) to obtain 93 ml of a cell suspension containing about $10^6$ spleen cells/ml.

Then, 0.2 ml each of the cell suspension was inoculated into each well of a 96-well microplate (Falcon 3072; from FALCON) and cultured at 37° C. under the air containing 5 v/v % of $CO_2$. In order to attain a sufficient growth of the hybridomas, the culture was continued for total 10 days including an exchange of the whole culture medium in each well for a fresh HAT medium (0.2 ml/well) on the 4th day of the culture.

Then, according to the method described below, the culture supernate of each well (hereinafter referred to as the "culture supernate A") was examined by a solid-phase method utilizing a procollagenase as an immobilized antigen and an enzyme-labeled second antibody to select the wells in which anti-procollagenase antibodies were being produced, and thus the hybridomas producing anti-procollagenase antibodies were selected.

Method for the Selection of the Anti-procollagenase Producing Hybridomas By a Solid-phase Method Using an Enzyme-labeled Second Antibody:

The purified procollagenase obtained in (1) above was diluted to 1 μg/ml with a 0.05M sodium carbonate-sodium bicarbonate buffer solution (pH 9.6). 100 μl each of the solution was injected into each well of a 96-well microplate (Immulon 600, from GREINER) and allowed to stand overnight at 4° C. to immobilize the procollagenase in each well. After washing each well with T-PBS, 300 μl of a PBS (pH 7.4) containing 0.5 w/v % of BSA was added and allowed to stand for 1 hour at room temperature, and then the supernate was removed. Each of the above culture supernate A was diluted twofold with a PBS (pH 7.4) containing 0.1 w/v % of BSA, and 100 μl of this solution was added, allowed to react for 2 hours at room temperature, and the well was washed with T-PBS (pH 7.4).

Then, biotin-labeled anti-mouse immunoglobulin (from ZYMED) was diluted to 5 μg/ml with a PBS (pH 7.4) containing 0.1 w/v % of BSA, and 100 μl each of this solution was added in each well, allowed to react for 1 hour at room temperature, and the well was washed with T-PBS (pH 7.4).

Then, streptavidin-peroxidase (from AMERSHAM) was diluted 1000 times with a PBS (pH 7.4) containing 0.1 w/v % of BSA, and 100 μl each of the solution was added in each well, allowed to react for 30 minutes at room temperature, and the well was washed with T-PBS (pH 7.4).

Then 100 μl each of a 0.15M citric acid-sodium phosphate buffer solution (pH 5.0) containing hydrogen peroxide and o-phenylenediamine (the former; 0.015 w/v %, the latter; 0.2 mg/ml) was added in each well and allowed to react for 5 minutes at room temperature.

Then, 50 μl each of 5N sulfuric acid was added in each well to stop the reaction (the obtained solution hereinafter referred to as "the test solution T").

Meanwhile, a control solution C was obtained according to the same procedure as described above except that HAT medium was added instead of the culture supernate A.

The absorbance at 492 nm of the test solution T and the control solution C was measured, respectively, using a Corona 2-wavelength microplate photometer (MTP-22, from CORONA DENKI K.K.). Thus, 21 wells were selected which gave the test solution T exhibiting higher absorbance than that of the control solution C by at least 0.1.

(5) Cloning and selection of the hybridomas

The hybridomas in the above wells were cloned by limiting dilution method.

The hybridomas in the wells selected in (4) above and thymus cells from BALB/c mice (obtained from 6 weeks old BALB/c mice according to a conventional method) were suspended in HAT medium to prepare a mixed cell suspensions containing 3 hybridoma cells/ml and $3 \times 10^6$ thymus cells/ml. 0.2 ml each of the suspensions was injected into each well of a 96-well microplate (Falcon 3072) and cultured for 14 days at 37° C. under the air containing 5 v/v % of $CO_2$. The culture supernate in the wells in which one colony/well was formed and a good proliferation of cells was exhibited was measured for the absorbance at 492 nm according to a similar procedure to the solid-phase method in (4) above utilizing an enzyme-labeled second antibody. And the wells exhibiting absorbance (A 492) of at least 0.3 were selected. Thus obtained were 14 clones of the hybridomas which produce anti-procollagenase monoclonal antibodies. The absorbance is shown in Table 2.

The monoclonal antibodies produced by thus obtained 14 clones of hybridomas are called K2F7, K5E1, K1C2, K1E6, K1F12, K2C3, K3B$_2$, K3F10, K4, K4B4, K4F5, K4H11, K5D1, K5G5 and K1D8, respectively.

TABLE 2

| Monoclonal antibody | Reactivity (Absorbance A492) |
| --- | --- |
| K2F7 | 0.417 |
| K5E1 | 0.839 |
| K1C2 | 1.097 |
| K1E6 | 0.401 |
| K1F12 | 1.355 |
| K2C3 | 0.402 |
| K3B2 | 0.638 |
| K3F10 | 0.643 |
| K4B4 | 0.312 |
| K4F5 | 0.559 |
| K4H11 | 1.395 |
| K5D1 | 0.377 |
| K5G5 | 0.587 |
| K1D8 | 0.552 |

$10^5$ cells each of the above hybridomas in the HAT medium were transferred to 5 ml of a HT medium (an RPMI 1640 medium containing 100 μM of hypoxanthine, 16 μM of thymidine and 10 v/v % of fetal bovine serum) and cultured for 14 days at 37° C. under the air containing 5 v/v % of $CO_2$, then transferred to 100 ml of an RPMI medium containing 10 v/v % of bovine fetal serum and cultured for 14 days at 37° C. under the air containing 5 v/v % of $CO_2$.

(6) Production and selection of the monoclonal antibodies 0.5 ml each of pristane (2, 6, 10, 14-tetramethylpentadecane) was administered in the peritoneal cavity of BALB/c mice (9 weeks old).

3 weeks later, the above 14 clones of hybridomas were suspended in an RPMI 1640 medium containing 10 v/v % of fetal bovine serum (about $2 \times 10^7$ cells/ml), and 0.5 ml each of the suspensions was administered in the peritoneal cavity of the mice.

Later, about 10 ml each of ascites deposited was collected and centrifuged (1000 rpm, 10 minutes) to precipitate the cell component to obtain the ascites supernate. To this was added a ⅔ volume of the saturated ammonium sulfate aqueous solution and the mixture was stirred for 1 hour at room temperature, allowed to stand for 1 hour at the same temperature, centrifuged at 10000 rpm for 20 minutes at 4° C., and the supernate was discarded to obtain the precipitate.

The precipitate was dissolved by the addition of the same volume of a 0.9 w/v % saline as that of the ascites supernate, centrifuged at 10000 rpm for 20 minutes at 4° C. to obtain the supernate. To the supernate was added a saturated ammonium sulfate aqueous solution in half a volume of that of the aforementioned ascites supernate, and the mixture was stirred for 1 hour at room temperature, allowed to stand for 1 hour at the same temperature, centrifuged at 10000 rpm for 20 minutes at 4° C., and the supernate was discarded to obtain the precipitate.

Then, the precipitate was dissolved in the equivalent volume of PBS (pH 7.4 ) to that of the aforementioned ascites supernate, dialyzed for 16 hours at 4° C. against 3000 ml of PBS (pH 7.4 ) to obtain the solutions of the 14 monoclonal antibodies.

The immunoglobulin class, subclass and L-chain isotype of each of the monoclonal antibodies were determined according to the aforementioned method, and the collagenase inhibiting activity of each monoclonal antibody was measured. And by selecting monoclonal antibodies which belong to immunoglobulin class and subclass $G_1$, whose L-chain isotype is kappa and which have a collagenase inhibiting activity, 11 monoclonal antibodies of the present invention were obtained.

The yield (antibody volume, protein concentration), immunoglobulin class and subclass, L-chain isotype and 50% collagenase inhibiting activity ($IC_{50}$) of the 11 monoclonal antibodies of the present invention are shown in Table 3.

Besides, among the 14 monoclonal antibodies mentioned above, 2 monoclonal antibodies (K1E6 and K5D1) exhibited a collagenase inhibiting activity ($IC_{50}$ was 1470 ng/ml. and 27.8 ng/ml, respectively), but their immunoglobulin class, subclass and L-chain isotype was M/kappa and $G_{2a}$/kappa, respectively. On the other hand, among the 14 monoclonal antibodies mentioned above, 1 monoclonal antibody (K1D8) did not exhibit a collagenase inhibiting activity, while its immunoglobulin class, subclass and L-chain isotype was $G_1$/kappa.

TABLE 3

| Monoclonal antibody | Yield | | Immunoglobulin class and subclass/ L-chain isotype | Collagenase inhibiting activity IC$_{50}$ (ng/ml) |
| --- | --- | --- | --- | --- |
| | Volume (ml) | Protein concentration (mg/ml) | | |
| K5E1 | 7.5 | 6.1 | G$_1$/kappa | 2.5 |
| K2F7 | 7.9 | 6.1 | G$_1$/kappa | 2.7 |
| K1C2 | 9.4 | 5.1 | G$_1$/kappa | 830 |
| K1F12 | 7.1 | 8.5 | G$_1$/kappa | 10.6 |
| K2C3 | 9.6 | 8.1 | G$_1$/kappa | 5.4 |
| K3B2 | 12.2 | 7.0 | G$_1$/kappa | 1.9 |
| K3F10 | 8.8 | 8.6 | G$_1$/kappa | 25.0 |
| K4B4 | 8.3 | 9.7 | G$_1$/kappa | 59.5 |
| K4F5 | 5.2 | 7.5 | G$_1$/kappa | 5.2 |
| K4H11 | 7.7 | 4.2 | G$_1$/kappa | 4.3 |
| K5G5 | 11.0 | 9.9 | G$_1$/kappa | 3.6 |

The K5E1-producing hybridoma indicated as "Anti-procollagenase monoclonal antibody (K5E1) producing hybridoma" and the K2F7-producing hybridoma indicated as "Anti-procollagenase monoclonal antibody (K2F7) producing hybridoma" were deposited with Fermentation Research Institute, Agency of Industrial Science and Technology. The accession number of the "Anti-procollagenase monoclonal antibody (K5E1) producing hybridoma" is FERM BP-2701, and the accession number of the "Anti-procollagenase monoclonal antibody (K2F7) producing hybridoma" is FERM BP-2700.

EXAMPLE 2

Assay of Procollagenase in the Serum of Cancer Patients and Normal Subjects:

(1) Preparation of immobilized antibodies

Each of the monoclonal antibody solutions of the present invention obtained in Example 1 was diluted to 5 µg/ml with a 0.05M sodium carbonate-sodium bicarbonate buffer solution (pH 9.6), and 100 µl each of the solution was injected into each well of a 96-well polystyrene microplate (Immulon 600). After allowed to stand overnight at 4° C., the well was washed with T-PBS (pH 7.4) to obtain an immobilized antibody fixed in the well of the microplate. (2) Preparation of labeled antibodies (biotinylated anti-procollagenase monoclonal antibodies)

Biotinylated anti-procollagenase monoclonal antibodies were prepared as follows according to the method described in Journal of Clinical Microbiology, 20, 109 (1984).

Each of the monoclonal antibody solutions of the present invention obtained in Example 1 was diluted to 1 mg/ml with a 0.1M sodium bicarbonate aqueous solution to obtain 1 ml each of the solutions. The solution was then dialyzed for 1 hour at room temperature against a 0.1M sodium bicarbonate aqueous solution to obtain an antibody solution with a pH of about 8.5.

Then, to 1 ml of the above antibody solution was added 0.06 ml of a solution of N-hydroxysuccinimidebiotin (from PIERCE) in DMSO (1 mg/ml), and the reaction was allowed for 4 hours at room temperature. The reaction mixture solution was dialyzed for 16 hours at 4° C. against 1000 ml of PBS (pH 7.4) to obtain about 1 ml each of the solutions of biotinylated anti-procollagenase monoclonal antibodies (about 1 mg/ml).

(3) Grouping of monoclonal antibodies recognizing mutually different epitopes

100 µl of the procollagenase solution in Example 1-(1) was diluted to 1 µg/ml with a 0.05M sodium carbonate-sodium bicarbonate buffer solution (pH 9.6), and 100 µl each of this solution was injected into each well of a 96-well microplate (Immulon 600) and allowed to stand overnight at 4° C. After washing each well with T-PBS (pH 7.4), 300 µl of a PBS (pH 7.4) containing 0.5 w/v % of BSA was added and allowed to stand for 1 hour at room temperature, and the supernate was removed.

Then, 50 µl of one of the diluted solutions of the monoclonal antibodies [200 µg/ml; prepared by diluting the monoclonal antibody solutions of Example 1 with a PBS (pH 7.4) containing 0.1 w/w % of BSA] and 50 µl of one of diluted solutions of the biotin-labeled antibodies [10 µg/ml; prepared by diluting the biotinylated anti-procollagenase monoclonal antibodies of (2) above with a PBS (pH 7.4) containing 0.1 w/v % of BSA] were simultaneously added in each well, allowed to react for 2 hours at room temperature, and the well was washed with T-PBS (pH 7.4).

Then, streptavidin-peroxidase (from AMERSHAM) was diluted 1000 times with a PBS (pH 7.4) containing 0.1 w/v % of BSA, and 100 µl each of this solution was added into each well, allowed to react for 30 minutes at room temperature, and the well was washed with T-PBS (pH 7.4).

Then, 100 µl of a 0.15M citric acid-sodium phosphate buffer solution (pH 5.0) containing hydrogen peroxide and o-phenylenediamine (the former; 0.015 w/v %, the latter; 0.2 mg/ml) was added into each well, and allowed to react for 5 minutes at room temperature.

Then, 50 µl of 5N sulfuric acid was added into each well to stop the reaction, and the absorbance at 492 nm was measured using a Corona 2-wavelength microplate photometer (MTP-22; from CORONA DENKI K.K.). The combinations of the monoclonal antibodies that gave higher absorbance by at least 0.1 than the absorbance observed when mutually identical monoclonal antibodies were reacted with each other (namely, when a monoclonal antibody and a labeled antibody prepared from the same monoclonal antibody were reacted) were judged to be the combinations of antibodies recognizing mutually different epitopes.

Consequently, the monoclonal antibodies were classified into the following 4 groups which recognize mutually different epitopes (antibodies included in a group recognize a same epitope).

Group 1 : K2C3, K2F7, K3B2, K4B4, K4F5, K5G5
Group 2 : K1C2, K4H11, K5E1
Group 3 : K1F12
Group 4 : K3F10

(4) Drawing of analytical curves for procollagenase assay by sandwich method and determination of combinations of an immobilized antibody and a labeled antibody that may give a good assay sensitivity.

Analytical curves for procollagenase assay by sandwich method were drawn as follows using an immobilized antibody and a biotinylated anti-procollagenase monoclonal antibody which were prepared from monoclonal antibodies classified to different groups mentioned above.

First, the procollagenase obtained in Example 1-(1) was subjected to twofold stepwise dilution from 100 ng/ml with a PBS (pH 7.4) containing 0.1 w/v % of BSA, and 100 µl each of these solutions was added to the immobilized antibody [that immobilized antibody fixed in the well of the microplate, which was prepared in a similar manner to (1) above] and allowed to react for 2 hours at room temperature, and the well was washed with T-PBS (pH 7.4).

Then, each of the biotinylated anti-procollagenase monoclonal antibodies was diluted to 5 µg/ml with a PBS (pH 7.4) containing 0.1 w/v % of BSA, and 100 µl of this solution was added into each well containing a immobilized antibody and allowed to react for 1 hour at room temperature, and the well was washed with T-PBS (pH 7.4).

Then, streptavidin-peroxidase (from AMERSHAM) was diluted 1000 times with a PBS (pH 7.4) containing 0.1 w/v % of BSA, and 100 µl each of this solution was added into each well, allowed to react for 30 minutes at room temperature, and the well was washed with T-PBS (pH 7.4).

Then, 100 µl of a 0.15M citric acid-sodium phosphate buffer solution (pH 5.0) containing hydrogen peroxide and o-phenylenediamine (the former; 0.015 w/v %, the latter; 0.2 mg/ml) was added into each well, and allowed to react for 5 minutes at room temperature.

Then, 50 µl of 5N sulfuric acid was added into each well to stop the reaction, and the absorbance of the reaction mixture at 492 nm was measured using a Corona 2-wavelength microplate photometer (MTP-22, from CORONA DENKI K.K.).

Then, analytical curves for assay of procollagenase were drawn taking absorbance on the axis of coordinates and procollagenase concentration on the axis of abscissas. As the result, it was found that one of the combinations of monoclonal antibodies which allow the most sensitive assay of procollagenase is the combination of K5E1 as an immobilized monoclonal antibody and K2F7 as a biotinylated anti-procollagenase monoclonal antibody. The combination allowed assay of procollagenase as low as 3.1 ng/ml. The analytical curve of this case is shown in FIG. 1.

In addition, by conducting an assay of a known amount of procollagenase by the same method as above except that the procollagenase was diluted with human serum (from GIBCO) instead of a PBS (pH 7.4) containing 0.1 w/v % of BSA, it was ascertained that the existance of human serum does not affect the assay of procollagenase.

(5) Assay of procollagenase in the serum from cancer patients and normal subjects by sandwich method 37 serum samples from 37 cancer patients and 31 serum samples from 31 normal subjects were measured for procollagenase concentration by sandwich method using K5E1 as an immobilized monoclonal antibody and K2F7 as an biotinylated anti-procollagenase monoclonal antibody.

First, 100 µl each of the serum was added to the immobilized antibody [an immobilized antibody in which K5E1 was fixed in the well of the microplate as described in (1) above], allowed to react for 2 hours at room temperature, and then the well was washed with T-PBS (pH 7.4).

Then, the well was successively reacted with biotinylated K2F7, streptavidin-peroxidase (from AMERSHAM), hydrogen peroxide and o-phenylenediamine, and the absorbance of the reaction mixture at 492 nm was measured in the same manner as that for the drawing of the analytical curves.

Then, based on the absorbance thus measured, the concentration of procollagenase in the reaction mixture was read from the analytical curve of FIG. 1 and the concentration of procollagenase in the serum was calculated.

The means and standard deviations of the concentration of procollagenase (ng/ml) in the serum from the cancer patients and the normal subjects are shown in table 4.

TABLE 4

| Sample | Procollagenase concentration | |
|---|---|---|
| | Mean (ng/ml) | Standard deviation |
| Serum from cancer patients (n = 37) | 28.99 | 36.50 |
| Serum from normal subjects (n = 31) | 9.11 | 6.67 |

The Cochran-Cox test demonstrated that the procollagenase concentration in the serum from the cancer patients was significantly (P<0.01) higher than that in the serum from the normal subjects. And, when the cutoff value was set at the sum (29.12 ng/ml) of the mean (9.11 ng/ml) and the threefold of the standard deviation of the procollagenase concentration in the serum from the normal subjects, 10 cases (27%) out of 37 were found positive in the cancer patients, whereas no positive cases were found in the normal subjects.

EXAMPLE 3

Screening of Cancer Patients by the Procollagenase Assay Method of the Present Invention Total 64 serum samples consisting of 60 samples from 60 cancer patients, whose cancer types were clinically specified, and 4 samples from 4 normal subjects were arranged at random so as to keep the operator blind to the source of each sample, and procollagenase concentration in each serum sample was determined according to the method described in Example 2-(5) to compare the values with those of the normal subjects obtained in Example 2-(5).

The samples were judged to be the serum from the cancer patients when they exhibited higher values than the cutoff value, i.e. the sum (29.12 ng/ml) of the mean plus the threefold of the standard deviation.

In addition, CEA concentration and CA19-9 concentration in the above samples were determined as controls using the commercially available kits for the assay of tumor markers, CEA.EIA II "Abbott" (from DAINABOT RADIOISOTOPE LAB., LTD.) and Immunoclone (trademark) CA19-9 (from FUJIREBIO, INC.), and judgement of cancer was conducted under the cutoff value of 5 ng/ml and 37 U/ml, respectively.

As the results, the number of the positive cases by the method of the present invention was 20 (33%) out of the 60 cancer patients, whereas no positive cases were observed in the normal subjects. Some positive cases were detected which the commercially available kits failed to detect.

Consequently, it is useful, as a complementing method for the conventional methods for diagnosing cancer, to measure serum procollagenase concentration (ng/ml) by the method of the present invention in the screening of cancer patients.

The results are shown in Table 5.

TABLE 5

| Clinical diagnosis | Judgement by the invention | Judgement by CEA | Judgement by CA 19-9 |
|---|---|---|---|
| Esophagus cancer | + | − | + |
| Stomach cancer | − | − | + |
| Stomach cancer | + | − | + |
| Stomach cancer | − | − | − |
| Stomach cancer | + | + | + |
| Stomach cancer | − | − | − |
| Stomach cancer | − | + | − |
| Stomach cancer | − | − | − |
| Stomach cancer | − | − | − |
| Stomach cancer | + | − | − |
| Stomach cancer | − | + | − |
| Stomach cancer | − | − | + |
| Stomach cancer | − | + | − |
| Stomach cancer | − | − | − |
| Stomach cancer | − | − | − |
| Stomach cancer | + | − | − |
| Stomach cancer | − | + | + |
| Stomach cancer | − | + | + |
| Stomach cancer | − | − | + |
| Stomach cancer | + | + | + |
| Stomach cancer | + | − | + |
| Stomach cancer | − | + | − |
| Large intestine cancer | − | − | − |
| Large intestine cancer | − | − | + |
| Large intestine cancer | + | − | + |
| Large intestine cancer | − | − | − |
| Large intestine cancer | + | − | − |
| Large intestine | − | − | + |

TABLE 5-continued

| Clinical diagnosis | Judgement by the invention | Judgement by CEA | Judgement by CA 19-9 |
|---|---|---|---|
| cancer | | | |
| Hepatoma | − | + | + |
| Hepatoma | − | − | + |
| Hepatoma | + | + | + |
| Gallbladder cancer | − | + | + |
| Gallbladder cancer | − | + | + |
| Gallduct cancer | − | − | + |
| Pancreas cancer | + | − | − |
| Lung cancer | + | − | − |
| Lung cancer | + | + | − |
| Nephroma | − | − | − |
| Nephroma | + | − | − |
| Nephroma | − | − | + |
| Bladder cancer | − | − | − |
| Ureter tumor | + | − | − |
| Ureter tumor | − | − | − |
| Ureter tumor | − | − | − |
| Prostatic cancer | − | − | − |
| Protstatic cancer | − | − | − |
| Prostatic cancer | − | + | − |
| Prostatic cancer | − | − | − |
| Mammary cancer | − | − | + |
| Mammary cancer | − | − | − |
| Cervix cancer | − | − | − |
| Cervix cancer | − | − | − |
| Cervix cancer | − | − | + |
| Ovarium cancer | + | + | + |
| Ovarium cancer | − | − | − |
| Ovarium cancer | − | − | + |
| Ovarium cancer | + | − | + |
| Ovarium cancer | + | − | + |
| Vulva cancer | + | − | − |
| Osteoma | + | + | + |
| Normal subject | − | − | − |
| Normal subject | − | − | − |
| Normal subject | − | − | − |
| Normal subject | − | − | − |

NB: "+" marks indicate "cancer" and "−" marks "non-cancer" as judged by each method for diagnosis.

EXAMPLE 4

Assay of Procollagenase in the Serum of RA Patients and OA Patients by the Method of the Present Invention Procollagenase concentration 14 serum samples from 14 RA patients and in 7 serum samples from 7 OA patients was determined in the same method as that described in Example 2-(5), and the values were compared with those obtained from the normal subjects in Example 2-(5).

The results are shown in Table 6.

TABLE 6

| Sample | Procollagenase concentration mean (ng/ml) | Standard deviation |
|---|---|---|
| Serum from RA patients (n = 14) | 47.81 | 50.14 |
| Serum from OA patients (n = 7) | 34.48 | 16.63 |
| Serum from RA + OA patients (N = 21) | 43.43 | 41.75 |
| Serum from normal subjects | 9.11 | 6.67 |

The Cochran-Cox test demonstrated that the procollagenase concentration in the serum from the RA patients and OA patients was significantly ($P<0.05$) higher than that in the serum from the normal subjects.

When the cutoff value was set at the sum (29.12 ng/ml) of the mean (9.11 ng/ml) plus the threefold of the standard deviation of the procollagenase concentration in the serum from the normal subjects, 8 cases (57%) out of 14 were found positive in the RA patients, and 5 cases (71%) out of 7 were found positive in the OA patients, whereas no positive cases were found in the normal subjects.

Industrial Applicability

By using the monoclonal antibody of the present invention, a simple and rapid assay of procollagenase by enzymeimmunoassay is allowed.

According to the assay of procollagenase in human serum by the assay method of the present invention, the procollagenase concentration in the serum from the cancer, RA and OA patients was found significantly higher than the procollagenase concentration in the serum from the normal subjects.

Therefore, it is beneficial to conduct assay of procollagenase concentration in human serum by the assay method of the present invention for diagnosing patients with elevated collagenase activity, such as patients of cancer, RA, OA etc.

We claim:

1. In a sandwich enzyme linked immunosorbent assay for determining the amount of procollagenase present in a human body fluid comprising the steps of contacting a sample of the body fluid with a first antibody immobilized on a solid phase and a second antibody labeled with an enzyme to form a complex, said first and second antibodies binding specifically to said procollagenase with a molecular weight of 52,000, whose corresponding collagenase cleaves Type I, Type II and Type III collagens, and determining the amount of said labeled second antibody bound to said complex, the improvement wherein said first and second antibodies are both a monoclonal antibody of the immunoglobulin class and subclass of $G_1$ having an L-chain of the Kappa isotype, and have a 50% inhibitory concentration of less than 10 ng/ml against said corresponding collagenase; said first and second antibodies recognize different epitopes of the procollagenase from each other; and wherein said first antibody is produced from a hybridoma of the accession number FERM BP-2701 and said second antibody is produced from a hybridoma of the accession number FERM BP-2700.

2. The sandwich enzyme linked immunosorbent assay method according to claim 1 further comprising the step of correlating the assay result to pathological conditions associated with increased levels of said procollagenase.

* * * * *